United States Patent [19]

Naono et al.

[11] 4,155,978

[45] May 22, 1979

[54] AUTOMATIC CHEMICAL ANALYZER

[75] Inventors: Toyohiko Naono; Tatsuo Hasegawa, both of Tokyo, Japan

[73] Assignee: Nihon Denshi Kabushiki Kaisha, Tokyo, Japan

[21] Appl. No.: 898,858

[22] Filed: Apr. 21, 1978

[51] Int. Cl.² .......................... G01N 33/16; G01N 1/14
[52] U.S. Cl. ........................................... 422/64; 422/81
[58] Field of Search .................. 23/253 R, 259, 230 R; 73/425.4 R; 422/64, 81

[56] References Cited

U.S. PATENT DOCUMENTS

| | | | |
|---|---|---|---|
| 3,762,879 | 10/1973 | Moran | 23/253 X |
| 3,764,268 | 10/1973 | Kosowsky et al. | 23/253 R |
| 3,881,872 | 5/1975 | Naono | 23/253 R |
| 3,883,305 | 5/1975 | Hoskins et al. | 23/253 R |
| 3,932,131 | 1/1976 | Rolfo-Fontana | 23/253 R |

*Primary Examiner*—R. E. Serwin

*Attorney, Agent, or Firm*—Webb, Burden, Robinson & Webb

[57] ABSTRACT

An automatic chemical analyzer comprising an extractor for extracting the desired sample from a plurality of liquid samples, a measuring valve for measuring out a fixed quantity of the extracted sample, a plurality of reagent storage tanks each storing a different kind of reagent according to the analysis intended, a plurality of reagent pumps equal in number to the number of reagent storage tanks, each of said plurality of reagent pumps being connected to each of said plurality of reagent storage tanks for drawing the reagents out of the reagent storage tanks, a reaction device comprising a plurality of reaction tubes for containing the samples and reagents, a reagent selector located between the pumps and the reaction device, said selector connecting a specific reagent pump to the reaction device according to the type of analysis.

5 Claims, 4 Drawing Figures

AUTOMATIC CHEMICAL ANALYZER

BACKGROUND

The subject invention relates to an automatic chemical anaylzer, and more particularly to an automatic chemical analyzer capable of changing from one reagent to another in the same channel.

Apparatus for continuously and automatically analyzing liquid samples such as blood, urine, etc. are presently available and are being used extensively in the clinical and chemical fields. In the larger type of apparatus in which many channels are provided, different analyses of the same sample can be carried out simultaneously. (See, for example my U.S. Pat. No. 3,881,872 entitled "Automatic Analyzing Apparatus.") However, in the more compact small-sized apparatus, a lesser number of channels, sometimes only a single channel, are provided. (See my application Ser. No. 666,921, filed Mar. 15, 1976, now U.S. Pat. No. 4,090,848.) If, for example, only one channel is provided and it is intended to carry out more than one type of analysis of a given sample, various operations such as selecting the measuring wavelength, washing the flow-through system, changing over the reagent, selecting the desired analyzing method, etc. will be necessary. Of these operations, reagent changeover is the most troublesome. This is because there is only one pump for a plurality of reagents housed in separate storage tanks, selection of one particular reagent or another being determined by a valve located between said tanks and said pump. In other words, after a given reagent has been force-fed into the reaction chamber through the action of the pump, it is necessary to wash not only the valve and associated feed lines connected to the reaction vessel but the pump also, before the next reagent can be sent to the reaction vessel. This indeed is very time consuming. Moreover, since the pump is difficult to clean, the chances of traces of the previous reagent remaining are likely so that when the next reagent is passed through, cross-contamination is a possibility. Another drawback with this arrangement is that reagent consumption is uneconomical, since it is necessary to displace reagent in a sufficient amount to reach the pump interior for each analysis.

One object of this invention is to provide an automatic chemical analyzer capable of shortening the washing time when changing over from one type of analysis to another.

Another object of this invention is to provide an automatic chemical analyzer capable of carrying out sampling without the adverse effect of cross-contamination.

A further object of this invention is to provide an automatic chemical analyzer capable of economic reagent utilization.

SUMMARY OF THE INVENTION

This invention relates to an automatic chemical analyzer having a device for extracting a liquid sample from a plurality of liquid sample containers, and a reaction device mixing the sample with selected reagents from a plurality of reagent storage tanks. Each reagent tank has associated therewith a pump for pumping reagent to the reaction device. A unique reagent selector is positioned between the pumps and the reaction device. The reaction device has associated therewith a light source, optical detecting means and data processing means for outputting a signal indicative of the mixture of the sample and the selected reactants. Preferably the reagent pumps are driven simultaneously from a common drive. This is possible due to the unique configuration of the reagent selector.

Preferably the reagent selector according to this invention comprises a nonrotatable hollow shaft, the interior of the shaft being in direct communication with the output of the selector. An annular valve block is fixed relative to the hollow shaft and is coaxial therewith. The valve block has a plurality of inlets and a plurality of equiangularly spaced outlet ports on a radial surface. The inlet and outlet ports are connected by ducts. A rotatable annular valve body is journaled on the hollow shaft and has a radial face which slides over the radial face of the annular valve block. The valve body has an inlet port on a radial face and an exposed outlet port. The inlet and outlet ports are connected by a single duct whereby rotation of the rotatable valve body can bring the inlet port thereof into registry with any one of the outlet ports of the annular valve block. A conduit associated with a rotary seal connects the outlet of the rotatable valve body to the interior of the hollow shaft. A platform or disk is fixed relative to the shaft and, of course the annular valve body, and generally lies in a plane perpendicular to the axis of the hollow shaft. A plurality of three-port control valves are equiangularly spaced on the platform. Each control valve has two positions: a first position connecting an inlet port to an outlet port, and a second position connecting the inlet port to a recirculation port. Conduits connect each outlet port of the three-port control valves to every other inlet port of the annular valve block. Conduits connect the remaining inlet ports on the annular valve block to a common source. Cams or other mechanical devices which turn with the rotatable annular valve body actuate the three-port control valves to place them in the first position when an associate inlet port of the annular valve block is in communication with the inlet port of the rotary valve body. The cams return the control valve to the second position when the rotating valve body moves from said registration. In other words, when the interior of the hollow shaft is placed in communication with the outlet port of a selected three-port direction control valve, that valve is placed in the first position, otherwise that valve is placed in the second position.

THE DRAWINGS

Still further objects and advantages of the subject invention will become more readily apparent by reading through the following detailed description in conjunction with the accompanying drawings of which;

DETAILED DESCRIPTION OF THE INVENTION

Figure 1:
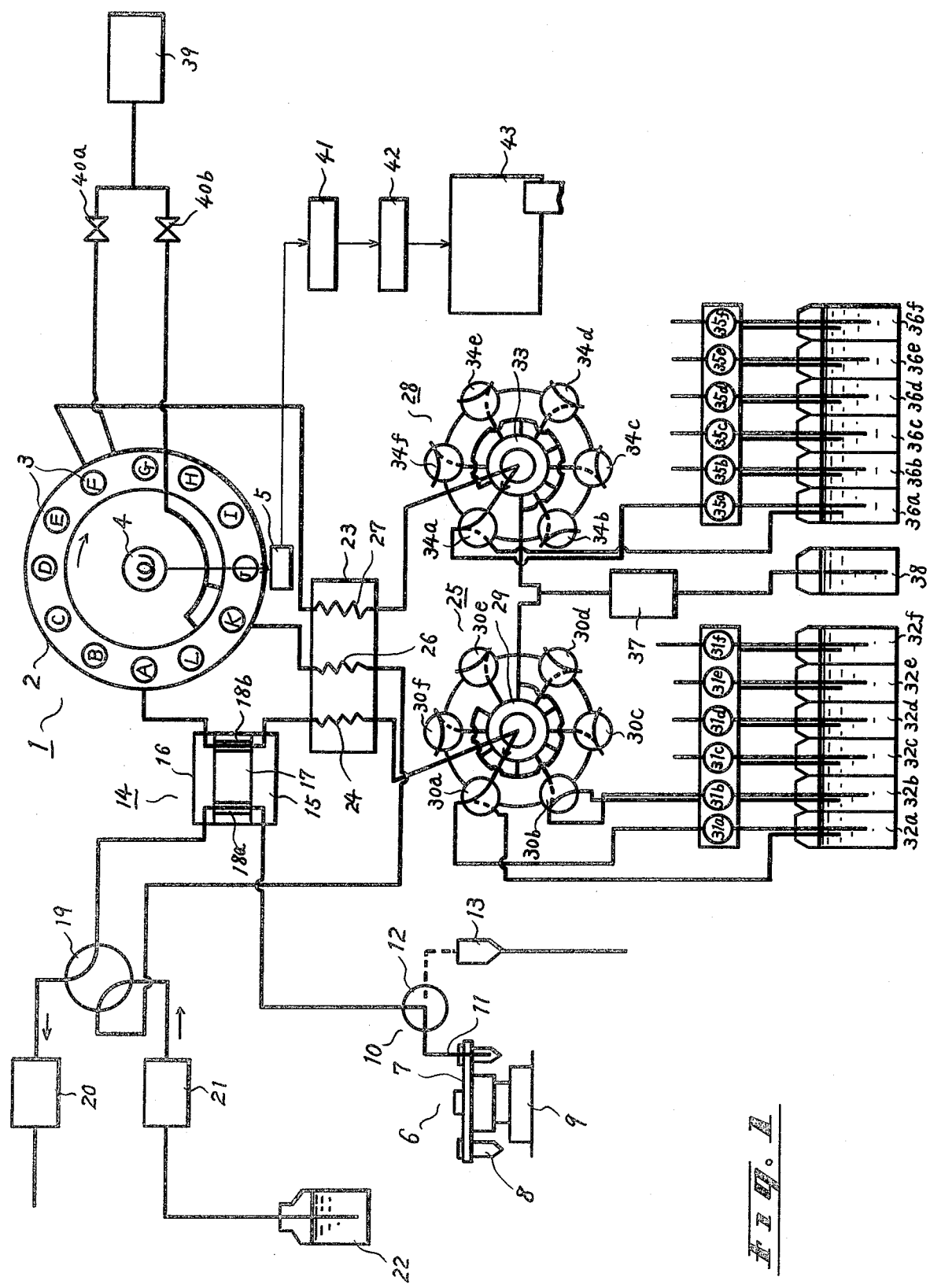
FIG. 1 shows one embodiment of this invention.

In FIG. 1, a reaction device 1 comprises a rotating body 2 equipped with holes for supporting a plurality of reaction tubes 3, said rotating body 2 being rotated intermittently by a geneva gear or the like. For details of this reaction device see my copending application Ser. No. 666,921, filed Mar. 15, 1976 now U.S. Pat. No. 4,090,848 entitled "Automatic Analyzing Apparatus." The positions of the various reaction tubes are represented by A, B, C . . . L. For example, the reaction tube positioned at A is supplied with sample together with a quantity of first reagent, and the reaction tube positioned at F is supplied with a quantity of second reagent. Further, the reaction tube positioned between F and G is supplied with gas so as to agitate and thereby thoroughly mix the sample and reagent, and the reaction tube positioned at J is irradiated with light from a lamp 4, the transmitted light being detected by a detector 5 so as to measure the absorbed light intensity. The position between J and K, and the K and L positions are the draining, washing, and washing solution draining positions, respectively.

A sample dispensing device 6 is comprised of a turntable 7 driven by a driving means 9, and a plurality of sample tubes 8 arranged around the periphery of said turntable 7. A sampling head 10 comprises a suction pipe 11 and a suction pipe shifting device 12. During operation, the shifting device 12 shifts the suction pipe 11 so that the tip of said suction pipe 11 enters the sample tube located at the sample sucking position. A quantity of sample is then sucked through the suction pipe. It is also possible to insert the suction pipe 11 into the wash tank 13, as shown by the broken line, so as to wash the tip. A sampling valve 14 comprises two fixed members 15 and 16, and a rotating member 17 housed between said two fixed members 15 and 16. The rotating member 17 is equipped with at least two passages 18a and 18b. The sampling head 10 is connected to the fixed member 15, and the fixed member 16 is connected to a changeover valve 19 which operates so as to connect pump 20 or pump 21 to said fixed member 16. When pump 20 is connected to the fixed member 16 (as shown in FIG. 1), liquid sample contained in the sample tube in which the tip of the suction pipe 11 is inserted is drawn into passage 18a provided in the rotating member 17. When the changeover valve 19 is in an alternate position connecting pump 21 to the fixed member 16, washing solution contained in the wash tank 22 is pushed through so as to flush out the entire sampling system. The fixed member 16 is also connected to the reaction tube positioned at A in the reaction device 1, and the fixed member 15 is also connected to the first reagent selector 25 via thru-pipe 24 which passes through a preheating block 23. Two passages 26 and 27 also pass through said preheating block 23. Of these, passage 26 carries the washing solution, pushed by pump 21 to the reaction tube located at K in the reaction device 1, and passage 27 connects a second reagent selector 28 to the reaction tube located at position F.

The first reagent selector 25 is comprised of a multiple port selector valve 29 and a plurality of three-port directional control valves 30a, 30b, 30c, 30d, 30e and 30f arranged around said selector valve 29, the changeover operation of said three-port control valves 30a–30f being interlocked with said selector valve 29. The three-port directional control valves have a stationary annulus 72 and 74 with ports and passages therein. A rotating disk or cylinder 76 with passages therein enables selectable interconnection of the passages in the stationary annulus. The input ports of said control valves 30a–30b are connected to the first reagent storage tanks 32a, 32b, 32c, 32d, 32e and 32f via pumps 31a, 31b, 31c, 31d, 31e and 31f, respectively. The output ports of each of said control valves are connected to the selector valve 29, and the recirculation ports of each said control valves are connected to respective return pipes for returning the reagent to the reagent storage tanks 32a–32f. That is to say, the reagent flow-through system is constructed and operates so that during analysis, only one control valve is connected to the selector valve 29 at any one time, while the other control valves are connected to the respective reagent return pipes.

In FIG. 1, control valve 30a is shown connected to selector valve 29. Accordingly, a quantity of first reagent is drawn out of storage tank 32a and enters one of the reaction tubes 3 via the first reagent selector 25. The pumps 31a–31f may each have their own independent driving means, or a single driving means can serve to operate all the pumps. In the former case, although each pump can be operated individually as required, the plurality of driving means increases the cost and size of the analyzer as a whole. On the other hand, in the latter case, although all the pumps are driven simultaneously, it does have an advantage in terms of cost and size. That is to say, a more compact and economically priced analyzer is feasible. The pumps may have a common drive because the outputs of the control valves not presently connected to the selector valve 29 are not blocked but the valves are connected for recirculation to the respective reagent storage tanks.

A second reagent selector 28, identical in construction to the first reagent selector 25, is provided. As in the case of the first reagent selector 25, the three-port control valves 34a–34f, arranged around a multiport selector valve 33, are connected to reagent storage tanks 36a–36f (designated, in this case, as second reagent storage tanks) via pumps 35a–35f. The second reagent flow path and its operation are also the same as that of the first reagent selector. As shown by FIG. 1, reagent from the second reagent storage tank 36a enters the reaction tube, located at the F position in the reaction device 1, via changeover valve 34a. A pump 37 draws the washing solution contained in tank 38 into the selector valves 29 and 33. Each of said selector valves 29 and 33 is equipped with a plurality, for example, twelve equiangularly spaced inlets in an annular valve block and associated passageways 47, every other inlet of said inlets being connected to the washing circuit, the remaining inlets being connected to the three-port control valves 30a–30f and 34a–34f, respectively for reagent supply purposes. A disk or body 55 which rotates relative to the annular valve block 47 has one passage and outlet port connectable by rotation to a selected one of the twelve outlet ports in valve block 47 through said associated passageways. By so doing, the passage in said rotating body is automatically washed during each reagent changeover.

A compressor 39 supplies compressed air via valves 40a and 40b to the reaction tube positioned midway between F and G (for stirring purposes), and the reaction tube positioned midway between J and K, and K and L (for draining purposes).

An amplifier 41 for amplifying the signal outputted by the light detector 5, and A-D converter 42 for converting the amplified output from the amplifier 41 into a digital signal, and a computer 43 for data analyzing the digitalized output of said A-D converter 42 function to output a signal indicative of the reaction products of the sample and reagents.

Figure 2:
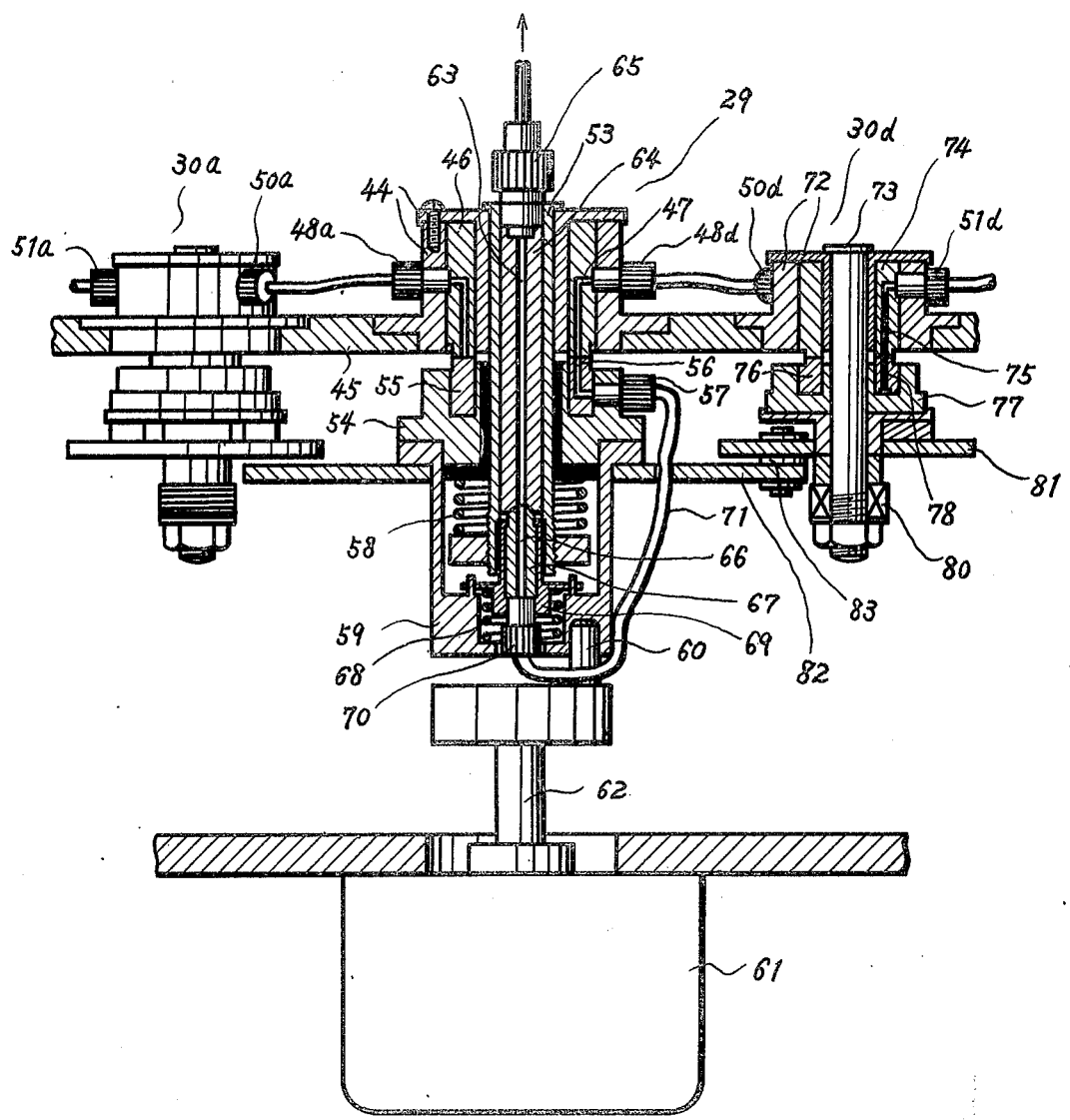
FIG. 2 shows the reagent selector used in the embodiment according to FIG. 1.
Figure 3:
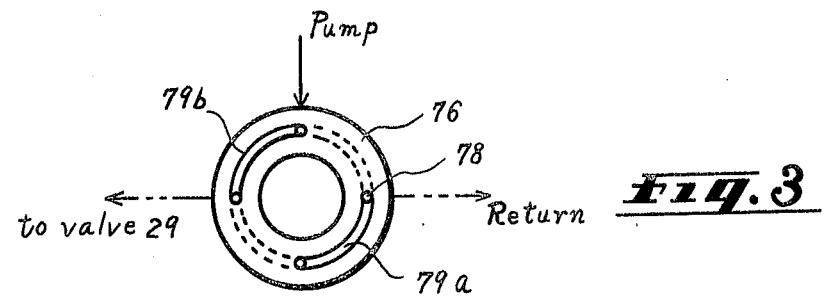
FIG. 3 shows the rotating block of the directional control valves shown in FIG. 2.
Figure 4:
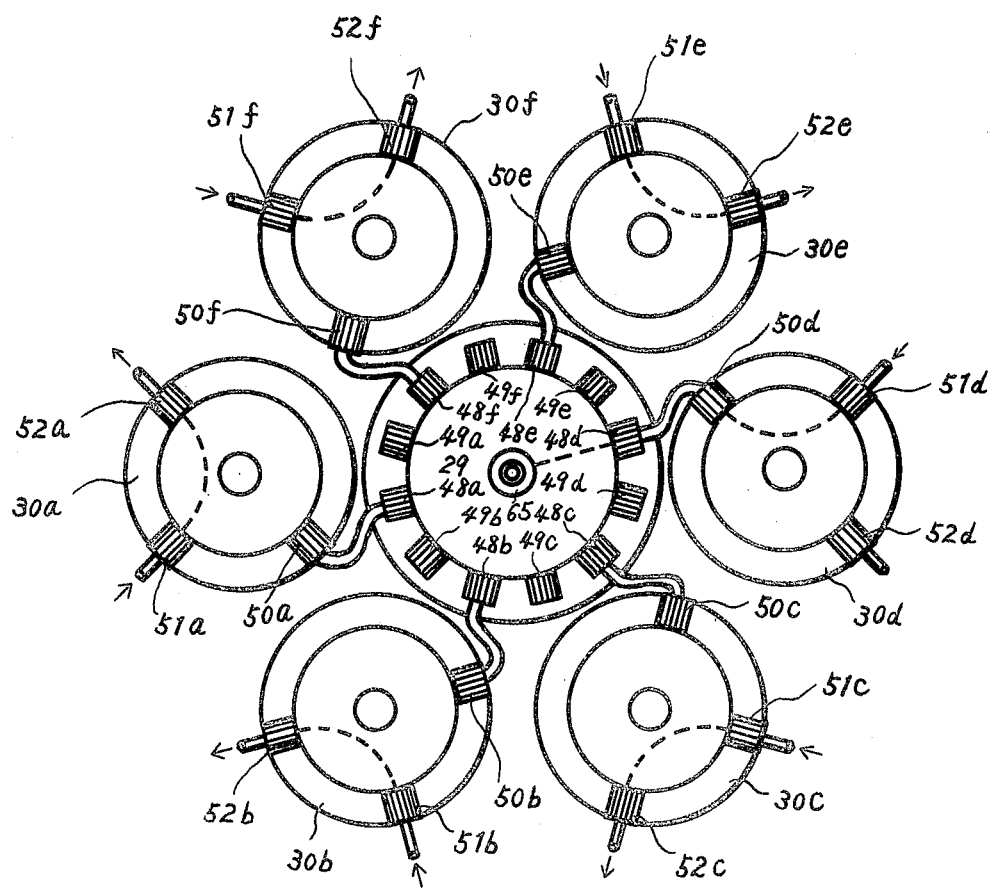
FIG. 4 shows the relation between the selector valve and the control valves.

FIGS. 2 to 4 show one embodiment, by way of example only, of the first and second reagent selector 25 or 28. Referring to the figures, a flanged base plate 45 for supporting the control valves 30a–30f equiangularly around the valve 29, and a fixed frame 44 (forming an integral part of the valve 29) is secured to the base plate 45. A fixed body 46 formed from an anti-corrosive and anti-erosive material such a P.T.F.E. (TEFLON) is held by the fixed frame 44. The frame 45 and body 46 comprise an annular valve block.

The fixed body 46 is provided with twelve (more or less) passageways or ducts 47, one opening of said ducts being connected to connectors 48a–48f and 49a–49f (See FIG. 4) built into the fixed frame 44, respectively, the other opening of said ducts leading out through the radial face or base of said fixed body 46, said respective openings describing a circle having a specific radius. Connectors 48a–48f and 49a–49f are arranged alternately around the fixed frame 44 as shown in FIG. 4. Of these two sets of connectors, e.g., 48a–48f are connected to connectors 50a–50f, which constitute the reagent outlet flow paths of control valves 30a–30f, respectively; whereas connectors 49a–49f are connected to the washing solution feed pump 37 as shown in FIG. 1.

Connectors 51a–51f, which constitute the reagent inlet flow paths of said control valves 30a–30f, are connected to reagent feed pumps 31a–31f, and connectors 52a–52f are connected to return pipes so as to return the reagent to the reagent storage tanks 32a–32f, respectively.

A hollow shaft 53 is held securely in the frame 44. A rotating frame 54 rotates around said shaft 53. A block 55, held and supported by said rotating frame 54, rotates together therewith. The block 55 is provided with a single duct 56, the upper opening of said duct 56 being arranged on a circle having the same radius as that on which the ducts 47 are arranged, the other opening of said duct 56 being connected to a connector 57. The contact surface pressure of the rotating block 55 and the fixed body 46 is kept at an adequate degree by means of a spring 58, which acts so as to press said rotating block 55 up against said fixed body 46 via the shaft 53 and a bearing. The rotating frame 54 is rotated by a rotating member 59, said rotating member 59 being, in turn, driven by a driving means 61 via shaft 62 and a connector 60. A fixed seal 64 made of P.T.F.E. (TEFLON), for example, and equipped with a duct 63 running lengthways through its center, is arranged in the hollow shaft 53. A connector 65 is provided at the upper end of said fixed seal 64, said connector 65 being connected to the fixed member 15 forming part of the sampling valve 14, in the case of valve 25, and to the reaction tube positioned at F in the reaction device 1 (see FIG. 1), in the case of valve 28. At the lower end of the fixed seal 64, a rotating seal 67, has surface contact with said fixed seal 64 provided with a duct 66. The rotating seal is shaped so as to prevent liquid from leaking from the contact surface of the two seals when the rotating seal rotates. The necessary contact surface pressure between the fixed and rotating seals is maintained by means of a spring 68. A holding member 69, for holding the rotating seal 67, rotates together with the rotating member 59, said holding member 69 being arranged so as to shift said rotating seal 67 vertically with respect to the rotating member 59. A connector 70 is arranged at the base of the rotating seal 67, said connector 70 being connected to connector 57 by a pipe 71.

In the case of each three-port directional control valve, fixed frame 72 is secured to the base plate 45 and a shaft 73 is held securely and centrally in said fixed frame 72. A fixed valve block 74, made of P.T.F.E. (TEFLON), is held in said fixed frame, said fixed block 74 being equipped with at least three ducts 75 each of which are connected to joints 50d, 51d, and 52d, respectively. Another block 76 held by a rotating frame 77, said block 76 is provided with four equiangularly spaced ducts 78, one pair of which are connected by groove 79a, the other pair being interconnected by a groove 79b. (See, FIG. 3. The dashed lines indicate an alternate position and not hidden passages.) The necessary surface pressure between said fixed block 74 and said rotating block 76 is provided by means of a spring 80. The rotating frame 77 is secured to a cross-shaped cam follower 81. The cam follower 81 may be brought into contact with a driving disk or cam 82, which is secured to the rotating member 59. Two pins 83 secured to cam 82 are located at an angular distance of, let's say 60° so as to drive two cams associated with two control valves simultaneuously. By so doing, the leading pin changes over, let's say, valve 30d so as to connect joints 50d and 51d, while the lagging pin changes over valve 30c so as to connect joints 51c and 52c. In other words, the leading pin rotates the valve, say, 90° in one direction and the lagging pin rotates the control valves, say 90° in the other direction. Accordingly, only one changeover valve can be connected to any one flow path of the selector valve at any one time.

In the above described configuration, by driving the driving means 61 in accordance with a preset program, selector valve 29 is rotated so as to link up with a specific pump via any one of the valves (30a–30f) as desired.

In the subject invention heretofore described in detail, since each reagent has its own exclusive pump and reagent selection valves are provided between said pumps and a plurality of reaction tubes, it is possible to repeatedly convey reagent to said reaction tubes without having to wash the pumps. Thus, the overall washing time is shortened and the problem of cross-contamination is resolved. Further, when changing over from one type of analysis to another, since it is not necessary to fill the flow system with fresh reagent as in the case of the prior art, reagent utilization is much more economical.

Other embodiments of the subject invention are feasible. For example, the reaction device does not necessarily have to be circular and there is no limit on the number of control valves and reagents used.

Having this defined my invention in the detail and with the particularlity as required by the Patent Office, what is desired protected by Letters Patent is set forth in the claims.

We claim:

1. An automatic chemical analyzer comprising a means for extracting the desired sample from a plurality of liquid samples, a means for measuring out a fixed quantity of said extracted sample, a plurality of reagent storage tanks, each storing a reagent according to the analysis intended, a plurality of pumps for drawing said reagents out of said reagent storage tanks, said plurality of pumps driven by one common driving means simultaneously each of said plurality of pumps being connected to one of said plurality of reagent storage tanks, a reaction device comprising a plurality of reaction tubes for containing a mixture of said samples and reagents, a reagent selecting means located between said pumps and said reaction device, an optical detecting means for detecting the amount of light passing through the mixture and producing a signal indicative thereof, a data processing means for processing the signals from said optical detecting means.

2. An automatic chemical analyzer comprising a means for extracting the desired sample from a plurality of liquid samples, a means for measuring out a fixed quantity of said extracted sample, a plurality of reagent storage tanks, each storing a reagent according to the analysis intended, a plurality of pumps for drawing said reagents out of said reagent storage tanks, each of said plurality of pumps being connected to one of said plurality of reagent storage tanks, a reaction device comprising a plurality of reaction tubes for containing a mixture of said samples and reagents, a reagent selecting means located between said pumps and said reaction device, said reagent selecting means being comprised of a multiple port selector valve equipped with an outlet connected to said reaction device, a plurality of inlets and a plurality of directional control valves, each of said plurality of directional control valves being equipped with an inlet and two outlets, said inlet being connected to one of said reagent storage tanks via a pump, one of said two outlets being connected to one of said inlets of said selector valve, the other of said two outlets being connected to said one reagent storage tank, an optical detecting means for detecting the amount of light passing through the mixture and producing a signal indicative thereof, and a data processing means for processing the signals from said optical detecting means.

3. An automatic chemical analyzer according to claim 2 in which said multiple port selector valve and said plurality of directional control valves are mounted on a common base plate, said plurality of control valves being arranged equiangularly around said multiple port selector valve, with the selector valve at the center.

4. An automatic chemical analyzer according to claim 2 in which said multiple port valve and said plurality of control valves are activated by a common driving means.

5. A multiple port selector useful in automatic chemical analyzers wherein each of a plurality of inputs is supplied by a reagent source with a pump and all pumps are driven simultaneously, said selector comprising:

a rotatable hollow shaft, the interior of the shaft being in direct communication with the outlet of a selector valve, an annular valve block fixed relative to the hollow shaft and coaxial therewith having a plurality of inlet ports and a plurality of equiangularly spaced outlet ports on a radial face, said inlet and outlet ports connected by ducts, a rotatable annular valve body journaled on the hollow shaft having a radial face which slides over said radial face of the annular valve block, said valve body having an inlet port on the radial face and an exposed outlet port, inlet and outlet ports being connected by a duct whereby rotation of the annular valve body can bring the inlet port thereof into registry with any one of the outlet ports of the annular valve block, means including a rotating seal for connecting the outlet of the rotatable valve body to the interior of the hollow shaft, a platform fixed relative to the shaft and being in a plane perpendicular to the axis thereof, a plurality of three-port control valves equiangularly spaced on said platform, each control valve having two positions, a first position connecting an inlet port to an outlet port, and a second position connecting said inlet port to a recirculation port, means for connecting each outlet port of the three-port control valves to every other inlet port of the annular valve body, means for connecting the remaining inlet ports on the annular valve body to a common source, means responsive to the rotation of the rotatable annular valve body for placing the control valves in the first position when the associated inlet port of the annular valve block is in communication with the outlet of said control valve and for returning the control valves to the second position.

* * * * *

UNITED STATES PATENT AND TRADEMARK OFFICE
CERTIFICATE OF CORRECTION

PATENT NO. : 4,155,978
DATED : May 22, 1979
INVENTOR(S) : Toyohiko Naono et al.

It is certified that error appears in the above-identified patent and that said Letters Patent are hereby corrected as shown below:

After the line listing the application serial number insert:

--Foreign Application Priority Data

April 27, 1977 Japan 52-48765--.

Signed and Sealed this

Fourteenth Day of August 1979

[SEAL]

Attest:

Attesting Officer

LUTRELLE F. PARKER
Acting Commissioner of Patents and Trademarks